United States Patent
Wu et al.

(10) Patent No.: US 6,824,499 B2
(45) Date of Patent: Nov. 30, 2004

(54) CONTROL CONSOLE AUTOMATICALLY PLANNING A PERSONAL EXERCISE PROGRAM IN ACCORDANCE WITH THE PHYSICAL CONDITION MEASURED THROUGH THE WHOLE EXERCISE SESSION

(76) Inventors: Peter Wu, No. 1, Lane 233, Sec. 2, Charng Long Rd., Taiping (TW), 411; Leao Wang, No. 1, Lane 233, Sec. 2, Charng Long Rd., Taiping (TW), 411

( * ) Notice: Subject to any disclaimer, the term of this patent is extended or adjusted under 35 U.S.C. 154(b) by 154 days.

(21) Appl. No.: 10/219,189

(22) Filed: Aug. 16, 2002

(65) Prior Publication Data

US 2004/0033862 A1 Feb. 19, 2004

(51) Int. Cl.[7] .............................................. A63B 21/00
(52) U.S. Cl. ................................ 482/8; 482/9; 482/900
(58) Field of Search ......................... 482/1–9, 900–902; 601/23

(56) References Cited

U.S. PATENT DOCUMENTS 5,853,351 A * 12/1998 Maruo et al. ................... 482/8
6,013,009 A * 1/2000 Karkanen ....................... 482/9
6,659,916 B1 * 12/2003 Shea ............................ 482/57

* cited by examiner

Primary Examiner—Glenn E. Richman
(74) Attorney, Agent, or Firm—Troxell Law Office PLLC; Kuo-Hsiung Chiu

(57) ABSTRACT

The present invention relates to a control console automatically planning a personal exercise program in accordance with the physical condition measured through the whole exercise session. The control console is in connection with a heartbeat detector for any fitness equipment. A microprocessor is fitted within the control console and used to record the related change and the interactive relationship of the heartbeat value under exercise parameters of distance, speed, duration and slope during the whole exercise session whenever the operator uses the electric treadmill. Therefore, the current physical state of the certain operator can be exactly detected so as to automatically plan an optimal exercise program according to the personal physical state. In addition, this program will be saved and used for next time when the operator uses the electric treadmill again. Meanwhile, the current physical condition will be measured again so as to renew another optimal exercise program for the certain operator.

6 Claims, 1 Drawing Sheet

CONTROL CONSOLE AUTOMATICALLY PLANNING A PERSONAL EXERCISE PROGRAM IN ACCORDANCE WITH THE PHYSICAL CONDITION MEASURED THROUGH THE WHOLE EXERCISE SESSION

BACKGROUND OF THE INVENTION

1. Fields of the Invention

The present invention relates to a control console used for an exercise equipment, and more particularly, to a device which effectively records the current physical condition of certain operators during the exercise session and plans an optimal exercise program in accordance with the personal physical condition. The measured data will be saved. When the operator uses the exercise equipment next time, the saved optimal exercise program will be performed first. In addition, the current physical condition will be renewedly measured so as to plan another optimal exercise program for the certain operator.

2. Description of the Prior Art

At present, the automatic planning and setting exercise program of the sports apparatuses are professionally oriented in order to provide the users with a more professional effect in exercise, rehabilitation and body-building. However, the automatic planning and setting of the sports apparatuses are dependent on the programming of the software of the control console. Therefore, an optimal exercise program for the operator is made after the personal data (e.g. age, sex or the desire consumption calories) are inputted, whereupon the sports apparatus is automatically activated to execute the planned exercise program.

The conventional control consoles are provided with many built-in exercise programs of simple design for the operators to choose one of them. For example, a microprocessor automatically controls the exercise time, speed, resistance or slope, etc. It's convenient and practical.

However, the built-in control program is in form of universal control mode and not necessarily meets the personal needs of all users. Therefore, a few personal details of the operator, such as age, sex, etc. can't represent the body type and the physical condition of the operator. If the calculation parameters of the basic program include only the data of age and sex, a considerable error will be produced. In brief, the exercise program created by the conventional control consoles doesn't meet the needs of each operator.

The so-called optimal "calorie consumption value" is a reference value suggested by the physicians or fitness trainers in accordance with the personal height and weight. However, the height and especially the weight of a person are not a constant value. Unless the user always takes care of the change of his height and weight or constantly gets the new suggestion of the optimal "calorie consumption value" from the physicians or fitness trainers, the optimal "calorie consumption value" will lose its reference value.

In addition, another conventional control console is provided with a heartbeat sensor. When the real heartbeat number sensed by the heartbeat sensor approaches to the preset maximal heartbeat value, a command is given to decelerate the motor to prevent from danger since the heartbeat number of the user is too high. However, the maximal heartbeat value is based on the age and the sex of a person or is a reference value suggested by physician which is variable according to the personal body type and the physical condition; therefore, its reference value is lost degree by degree.

SUMMARY OF THE INVENTION

It is a primary object of the present invention to eliminate the above-mentioned drawbacks and to provide a control console automatically planning a personal exercise program in accordance with the physical condition measured through the whole exercise session. Based upon the above-mentioned, the inventor of the present invention found after numerous trials that the only way to effectively eliminate the aforementioned drawbacks is to record the current exact physical state of certain operator through the whole exercise session. Accordingly, the exercise program most suitable for the operator can be settled. In addition, this settled exercise program will be used for another exercise session next time. Meanwhile, the current physical condition will be measured again so as to renew another optimal exercise program for the certain operator. This procedure always ensures an effective control of current physical state of the operator to renew a personal exercise program and gradually achieves the exercise effect in due order.

BRIEF DESCRIPTION OF THE DRAWINGS

The accomplishment of this and other objects of the invention will become apparent from the following description and its accompanying drawing of which.

DETAILED DESCRIPTION OF THE PREFERRED EMBODIMENT

Figure 1:
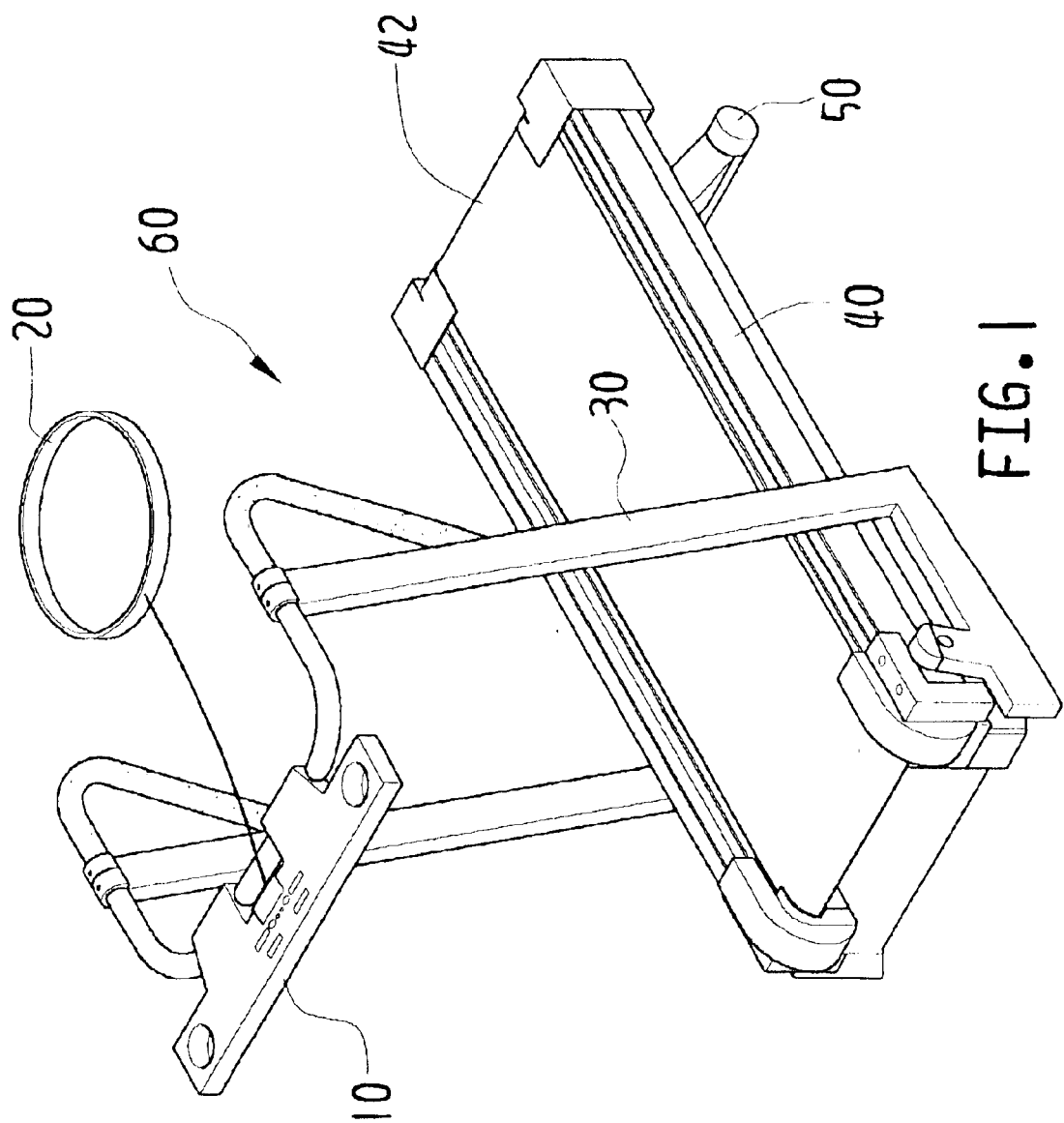
FIG. 1 is a perspective view of a treadmill with the application of the present invention.

First of all, referring to FIG. 1, the present invention is applied to an electric treadmill 60. The electric treadmill 60 includes a control console 10, a heartbeat detector 20, two handrails 30, a base frame 40 and a foot bar 50. The base frame 40 has a treadmill walking belt 42 driven by a motor (not shown). The operator can stand on the treadmill walking belt 42 to perform walking or jogging exercise. Besides, the control console 10 is connected with the heartbeat detector 20 so as to automatically control the motor's operation, including duration, rotational speed and slope. The heartbeat detector 20 is fastened around the breast or the wrist of the operator to detect heartbeat.

A microprocessor (not shown) is fitted within the control console 10 and used to record the related change and the interactive relationship of the heartbeat value under exercise parameters of distance, speed, duration and slope during the whole exercise session whenever the operator uses the electric treadmill 60. As a result, the current physical state of the certain operator can be exactly detected so as to automatically plan an optimal exercise program according to the personal physical state. And this program will be saved and used for next time first when the operator uses the electric treadmill 60 again. Meanwhile, the current physical condition will be measured again so as to renew another optimal exercise program for the certain operator.

Besides, the "record value through the whole exercise session" can take "measured value through the whole exercise session" as basic calculation parameter. Alternatively, the "time-division measured value" can also be taken as basic calculation parameter. This technical decision should belong to the scope of the present invention.

The microprocessor is driven by software program which doesn't belong to the scope of the present invention. Thus, no further description will be given hereinafter.

Furthermore, when an exercise program is created, a user's number is given by the built-in program of the microprocessor. Accordingly, the user has to remember the user's number. When he uses the electric treadmill 60 next time, it's only required to choose the user's number for performing the saved exercise program.

In brief the control console 10 of the present invention can be considered as an accompanying fitness trainer who always provides a most exact and suitable exercise session for the operators so as to gradually achieve the exercise effect in due order.

Many changes and modifications in the above-described embodiment of the invention can, of course, be carried out without departing from the scope thereof. Accordingly, to promote the progress in science and the useful arts, the invention is disclosed and is intended to be limited only by the scope of the appended claims.

What is claimed is:

1. A method for automatically planning a personal exercise program in accordance with the physical condition of an operator operating one exercise device and measured throughout an exercise session comprising the steps of:
    a) registering the operator by identifying and recording identifying information of the operator utilizing a control console connected to the exercise device and having a microprocessor, and attaching a heartbeat detector to one of a torso and an arm of the operator;
    b) measuring and recording heartbeat data of the operator during a current exercise session utilizing the heartbeat detector electrically connected to the control console;
    c) evaluating and adjusting the personal exercise program based on related changes and interactive relationships of heart beat values of the recorded heartbeat data of the current exercise session and previous exercise sessions to be recalled and used during a subsequent exercise program utilizing the control console; and
    d) controlling the exercise device during the subsequent exercise program to perform within operation parameters based on the personal exercise program by identifying the operator utilizing the control console.

2. The method according to claim 1, wherein operation parameters of the controlling step d) are selected from the group consisting of distance, speed, duration, and slope.

3. The method according to claim 1, wherein during the evaluating and adjusting step c) the personal exercise program is modified following each current exercise session and recorded for use during the subsequent exercise session.

4. A control system for automatically planning a personal exercise program in accordance with a physical condition of an operator operating one exercise device and measured throughout and exercise session and comprising:
    a) a control console connected to the exercise device and having a microprocessor identifying and recording identifying information of the operator; and
    b) a heartbeat detector attached to one of a torso and an arm of the operator, electrically connected to the control console for measuring to record heartbeat data of the operator during a current exercise session utilizing the heartbeat detector,
    wherein the control system evaluates and adjusts the personal exercise program based on related changes and interactive relationships of the heart beat values of the recorded heartbeat data of the current exercise session and previous exercise sessions to be recalled and used during a subsequent exercise program, and the control console controls the exercise device during the subsequent exercise program to perform within operation parameters based on the personal exercise program by identifying the operator.

5. The control system according to claim 4, wherein the control console controls operation parameters of the exercise device selected from the group consisting of distance, speed, duration, and slope.

6. The control system according to claim 4, wherein the control console modifies and records the personal exercise program during each current exercise session for use during the subsequent exercise session.

* * * * *